United States Patent [19]

Bourgeois

[11] Patent Number: 5,058,584
[45] Date of Patent: Oct. 22, 1991

[54] METHOD AND APPARATUS FOR EPIDURAL BURST STIMULATION FOR ANGINA PECTORIS

[75] Inventor: Ivan Bourgeois, Verviers, Belgium

[73] Assignee: Medtronic, Inc., Minneapolis, Minn.

[21] Appl. No.: 574,739

[22] Filed: Aug. 30, 1990

[51] Int. Cl.$^5$ .............................................. A61N 1/36
[52] U.S. Cl. ................................................... 128/421
[58] Field of Search ................. 128/419 R, 421, 42 R, 128/423 R

[56] References Cited

U.S. PATENT DOCUMENTS

| | | | |
|---|---|---|---|
| 3,572,345 | 3/1971 | Auphan | 128/419 R |
| 3,822,708 | 7/1974 | Zilber | 128/49 R |
| 4,019,518 | 4/1977 | Maver et al. | 128/419 R |
| 4,026,301 | 5/1977 | Friedman et al. | 128/421 |
| 4,044,774 | 8/1977 | Corbin et al. | 128/419 R |
| 4,669,477 | 6/1987 | Ober | 128/421 |

*Primary Examiner*—William E. Kamm
*Attorney, Agent, or Firm*—John L. Rooney

[57] ABSTRACT

Method of and apparatus for the treatment of angina pectoris using electrical stimulation within the epidural space of the spinal cord. A sensor is used to trigger stimulation only during periods of activity assumed to be symptomatic. The sensor may measure any of a number of parameters including blood oxygen saturation level or mechanical activity. In the preferred embodiment, a piezoelectric activity sensor is programmed to determine when the level of activity is reached at which angina is expected to occur in a particular patient. This determination is used to trigger an implantable pulse generator. Bursts of high frequency stimulation energy are applied by an insulated lead to electrodes implanted in the epidural space at an upper thoracic or lower cervical location. The increased neural activity caused by the stimulation bursts eliminates the pain sensation and allows an equal or higher exercise level of the patient without pain or at a similar pain level. The epidural stimulation does not decrease coronary perfusion at the same exercise level. When sensed body activity decreases below a second programmed level, electrical stimulation is inhibited.

7 Claims, 8 Drawing Sheets

5,058,584

METHOD AND APPARATUS FOR EPIDURAL BURST STIMULATION FOR ANGINA PECTORIS

CROSS REFERENCE TO CO-PENDING APPLICATIONS

U.S. patent application Ser. No. 07/490,065, filed Mar. 7, 1990, and entitled "Position Responsive Neuro Stimulator" is assigned to the assignee of the present invention.

BACKGROUND OF THE INVENTION

1. Field of the Invention

The present invention relates generally to medical devices, and more particularly, relates to implantable medical devices for the treatment of angina pectoris.

2. Description of the Prior Art

The high prevalence of angina pectoris in modern society is well documented. The current standard therapy usually relies upon nitroglycerine various vasodilators to increase perfusion and beta-blockers and other chemical agents to control coronary perfusion and pain. Normally surgical intervention or angioplasty is required to chronically increase profusion in those patients for whom such a procedure is indicated.

A newly discovered technique for angina patients involves electrical stimulation of the spinal cord. D. F. Murphy, et al. describe the clinical results of such a technique in "Dorsal Column Stimulation for Pain Relief from Intractable Angina Pectoris", Pain, Volume 28, 1987, at 363–368, incorporated herein by reference.

Though the clinical results reported by Murphy, et al. are most encouraging, it is very desirable for optimal pain control on an individual to vary the degree of electrical stimulation with the need of the patient.

SUMMARY OF THE INVENTION

The present invention overcomes the disadvantages of the prior art by providing a system and method for the treatment of angina pectoris using electrical stimulation of the spinal cord which varies with activity level of the patient. A chronically implantable sensor determines the relative activity level. Electrical stimulation is provided whenever the activity level exceeds a programmed threshold. An implantable pulse generator produces bursts of stimulation energy, which are applied to the upper spinal cord using an insulated lead. Electrodes implanted in the epidural space transfer the stimulation bursts to the spinal cord.

Whenever the patient is active, this condition is sensed by the implanted sensor, and the implanted pulse generator provides stimulation bursts to the spinal cord to block angina pain signals to the brain.

This causes, in comparison to the situation without stimulation, a modified balance of sympathetic and parasympathetic drive to the heart. Increased parasympathetic drive decreases peripheral resistance lowering the work load of the heart and requiring less perfusion (oxygen consumption). The heart becomes less ischemic. This has occurred during exercise when higher workloads, lower ST segment, longer times to angina pain and shorter recovery times have been observed when spinal cord stimulation is used.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
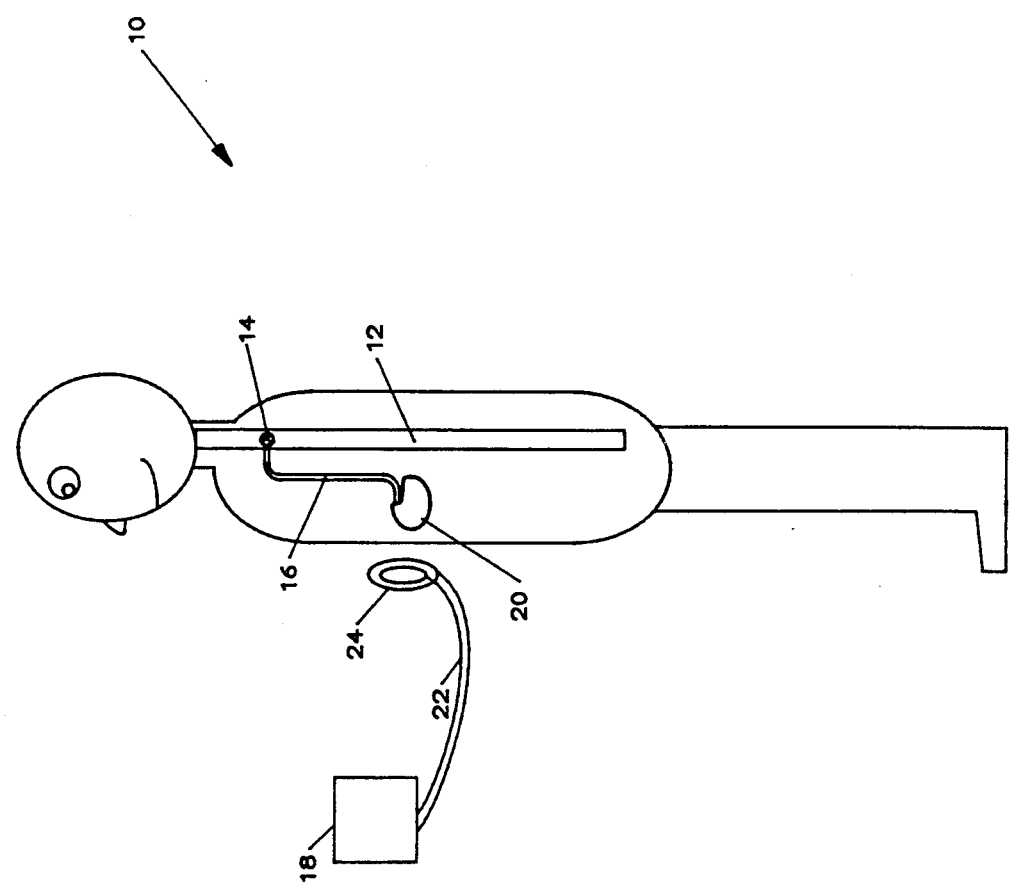
FIG. 1 is a schematic view of a patient having a chronically implanted system for the treatment of angina pectoris using electrical stimulation of the spinal cord.

FIG. 1 is a schematic diagram of a patient 10 having a chronically implanted system for the treatment of angina pectoris using electrical stimulation of the spinal cord. Electrode 14 is implanted in the epidural space of spinal column 12 as is shown below in greater detail. Electrode 14 is coupled to implantable pulse generator 20 by insulated lead 16. Implantable pulse generator 20 contains an activity sensor for determining relative activity level of patient 10.

The various operating parameters of implantable pulse generator 20 are adjustable by medical personnel using programmer 18. This permits pulse amplitude, number of pulses per burst, etc. to be modified after implant. Using programmer 18, the threshold is also set for minimum activity to cause generation of stimulation pulses. This threshold will vary from patient to patient and over time for a given patient. Also a switch-off activity threshold could be preprogrammed separately and/or a time after which the stimulation ceases when the activity falls below the shut-off activity threshold level. Alternatively, a fixed length burst can be generated as a result of crossing the turn-on threshold of activity. With current clinical knowledge, these thresholds must be determined empirically. Programmer 18 communicates with implantable pulse generator 20 via radio frequency energy transferred by RF cable 22 and radiated by antenna 24.

Figure 2:
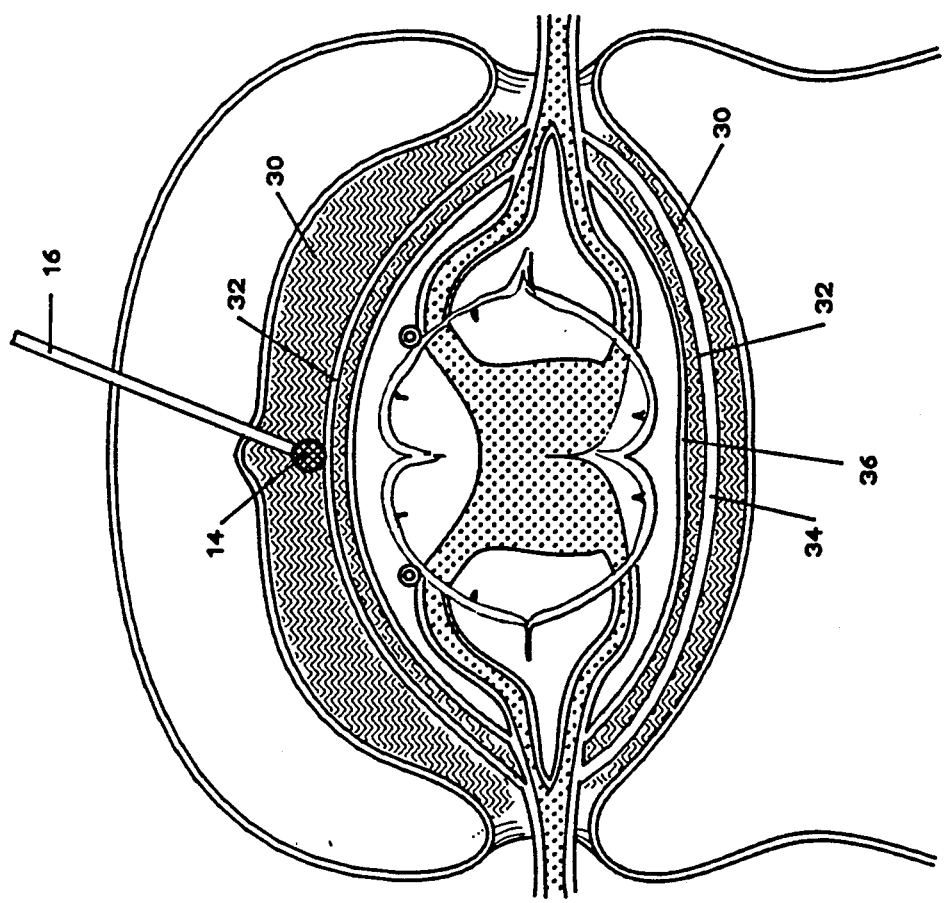
FIG. 2 is a cross sectional view of the spinal cord showing chronic implantation of the electrode.

FIG. 2 is a cross sectional view of the spinal cord of patient 10. Electrode 14 is preferably a PISCES SIGMA ® Model 3483 epidural electrode available from Medtronic, Inc. in Minneapolis, Minn. It is inserted into epidural space 30 as shown. Electrode 14 is coupled to implantable pulse generator 20 via insulated lead 16 (see also FIG. 1).

Preferably electrode 14 is implanted at an upper thoracic or lower cervical spinal level. Dura mater 32 is shown to provide orientation of electrode 14 within epidural space 30. Also shown are arachnoid 34 and subarachnoid space 36.

Figure 3A:
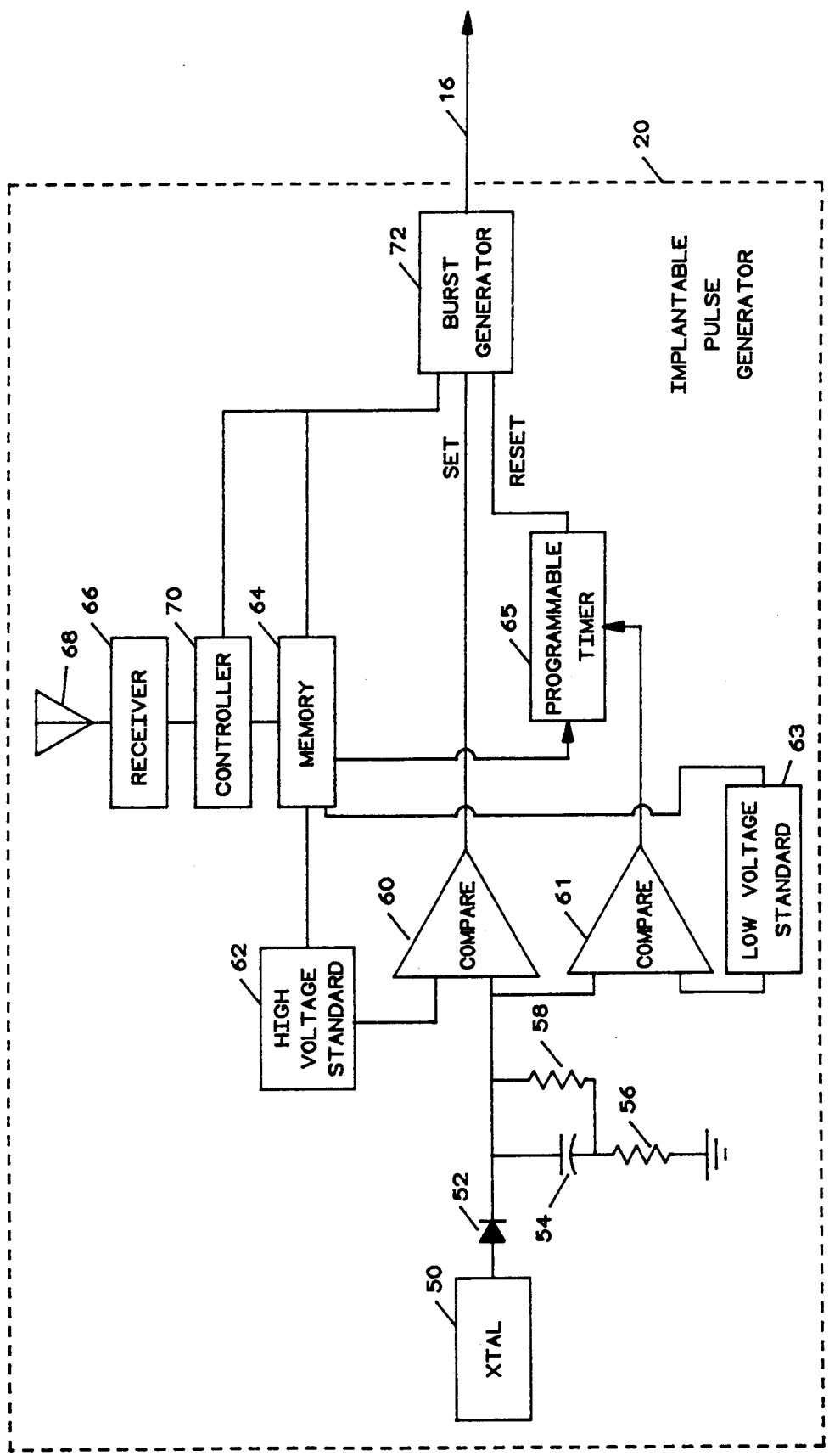
FIG. 3A is a block diagram of the implantable pulse generator of the present invention.

FIG. 3A is a block diagram of the electronic circuitry of implantable pulse generator 20. In the preferred embodiment, implantable pulse generator 20 is basically an Itrel II® neurological pulse generator also available from Medtronic, Inc. FIG. 3 presents most prominently those features not available in the commercially available device.

In the preferred embodiment, cardiac requirement is sensed by Xtal 50 which is a piezoelectric device. It is preferably mounted on the housing of implantable pulse generator 20 in the same manner as with the ACTIVI-TRAX® implantable pulse generator manufactured and sold by Medtronic, Inc. Xtal 50 generates a signal corresponding to the mechanical vibrations which impinge upon the housing of implantable pulse generator 20. The greater the activity of patient 10, the greater the energy of the mechanical vibrations impinging upon the housing of implantable pulse generator 20 and the greater the generated signal. Sensing of activity in this manner is by way of example only and is not to be limiting of the present invention. Other sensors, such as blood oxygen saturation, may also be employed.

The signal from Xtal 50 is rectified by diode 52. This rectified signal is integrated by capacitor 54 through resistor 56. Rate of integration is controlled by leakage resistor 58. Experience has shown that it is desirable to select these components to provide a pass band of about 10 hertz centered on 10 hertz.

The rectified and integrated signal is compared to the output of high voltage standard 62 by compare 60. This comparison determines whether the turn-on activity threshold is reached. To enable comparison against a variable threshold, high voltage standard 62 is programmable by the physician.

Similarly, compare 61 compares the integrated output with the output of low voltage standard 63. This comparison is used to determine when the activity drops below a lower turn-off activity threshold. The turn-on and turn-off activity thresholds are selected by programmer 18 (see also FIG. 1) and are received as a radio frequency signal on antenna 68. The radio frequency signal is demodulated by receiver 66 and sent as a digital quantity to controller 70 for storage in memory 64.

Memory 64 also stores the other parameters which control generation of the stimulation pulses, which are supplied to burst generator 72 as shown. The output of compare 60 is high whenever the activity signal exceeds the programmed turn-on activity threshold. It is this signal which sets burst generator 72 to produce a burst of stimulation pulses. Burst generator 72 is directly coupled to insulated lead 16. Whenever the activity signal drops below the programmed turn-off activity threshold, compare 61 resets the input of burst generator 72, thereby inhibiting output of stimulation pulses. Whenever the activity signal drops below the programmed turn-off activity threshold, compare 61 starts a programmable timer 65, which when it times out, resets the input of burst generator 72, thereby inhibiting output of stimulation pulses.

Alternatively, programmable timer 65 may be turned on at the same time as burst generator 72 is set. This may be accomplished by programming low voltage standard 63 to the same level as high voltage standard 62. This will result in the production of an output burst of fixed length triggered by sensed activity passing the turn-on threshold.

Figure 3B:
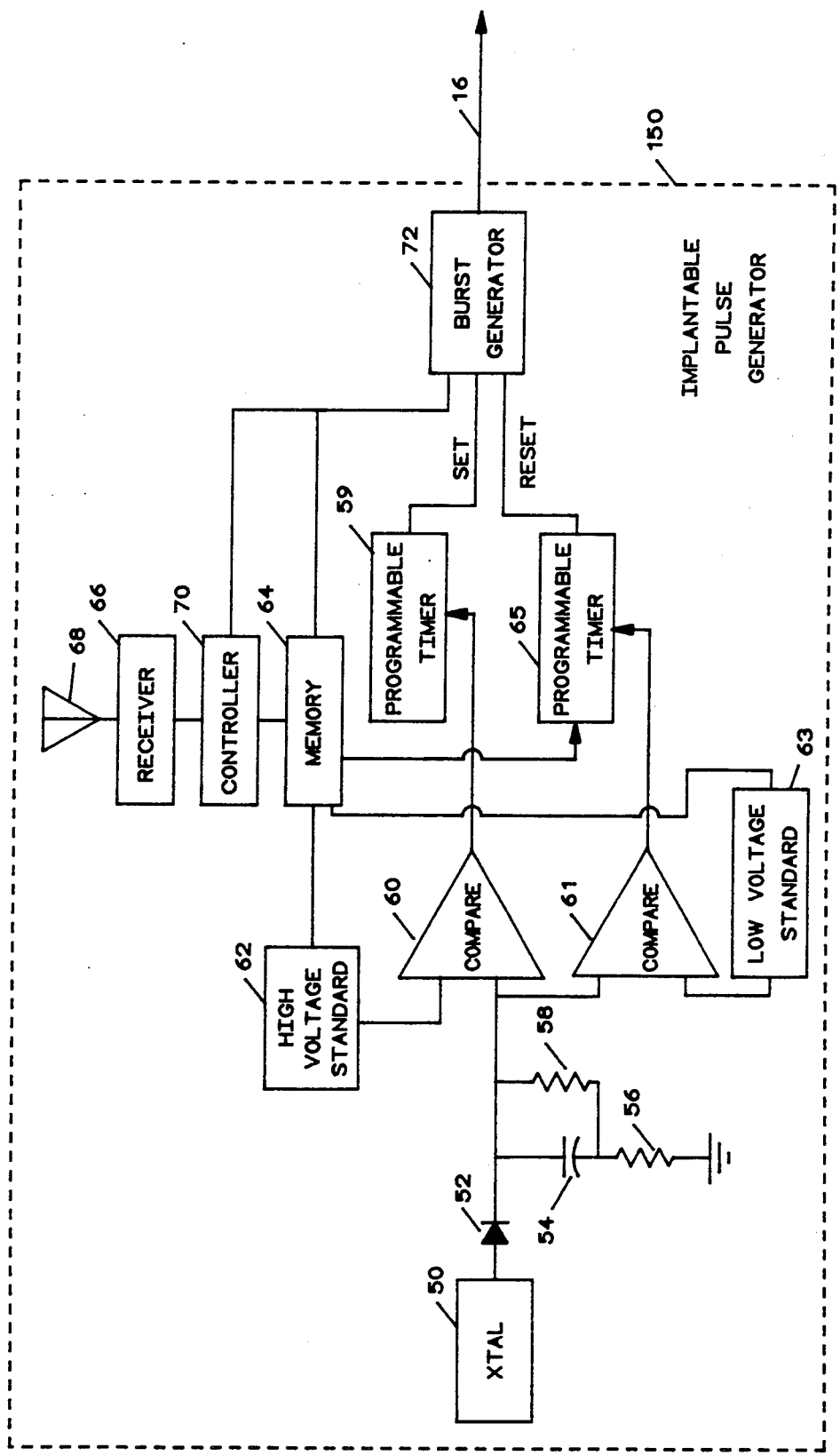
FIG. 3B is a block diagram of an alternative embodiment of the implantable pulse generator.

FIG. 3B is a block diagram of alternative embodiment implantable pulse generator 150. This circuit employs a second programmable timer 59 on the set input of burst generator 72. This provides a programmable delay before the turn on of stimulation pulses. The remainder of the elements are as previously described.

Figure 4A:
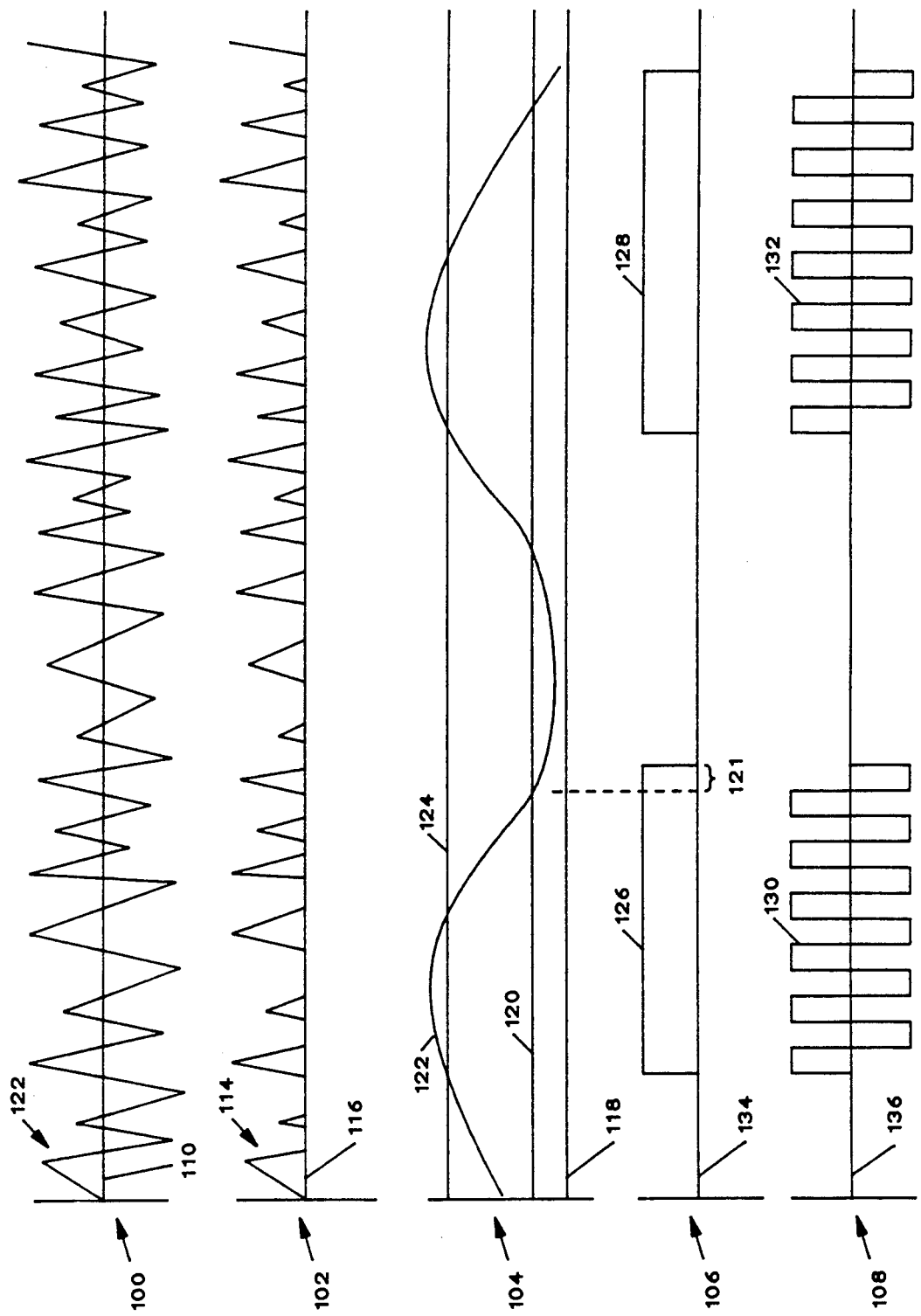
FIG. 4A is a graphical representation of the wave forms of various key signals within the implantable pulse generator.

FIG. 4A is a graphical representation of various key signals within implantable pulse generator 20. Wave form 100 shows the output of Xtal 50. It varies nearly randomly and is both positive and negative with respect to baseline 110. The amplitude and frequency of the signal directly responds to the impingement of mechanical energy on the housing of implantable pulse generator 20.

Wave form 102 shows signal 114 which is the same as signal 122 after half-wave rectification by diode 52. Notice that this signal is never negative with respect to baseline 116.

Wave form 104 shows the inputs to compare 60 and compare 61. All signals are positive with respect to baseline 118. Levels 120 and 124 represent turn-off and turn-on activity threshold levels, respectively. These are produced by low voltage standard 63 and high voltage standard 62 as discussed above. Wave form 122 shows the output of integrating capacitor 54. Notice that high voltage standard 62 is programmed to level 124 (i.e. a turn-on activity threshold), and while wave form 122 is below that threshold, no spinal cord stimulation occurs. Low voltage standard 63 is programmed to turn-off activity threshold level 120. As the current activity level (i.e. wave form 122) exceeds the programmed turn-on activity threshold (i.e., level 124) the spinal cord is stimulated. Stimulation continues until the activity level 122 falls below turn-off activity threshold level 120 when stimulation stops after the time period 121, determined stimulation stops after the time period 121, determined by programmable timer 65.

If low voltage standard 63 is programmed to the same level as high voltage standard 62, turn-off threshold level 120 and turn-on threshold level 124 are coincident. This produces the special case of a fixed length burst of time period 121 as determined by programmable timers 65

Wave form 106 shows the state of burst generator 72 for wave form 104. When the output of compare 60 is high, the trigger of burst generator 72 is set and remains set until reset by the output of compare 61 (see also FIG. 3). Trigger pulses 126 and 128 are positive with regard to baseline 134.

Wave form 108 shows the output of burst generator 72. Notice that high frequency burst 130 is keyed by trigger pulse 126 and high frequency burst 132 is keyed by trigger pulse 128.

Figure 4B:
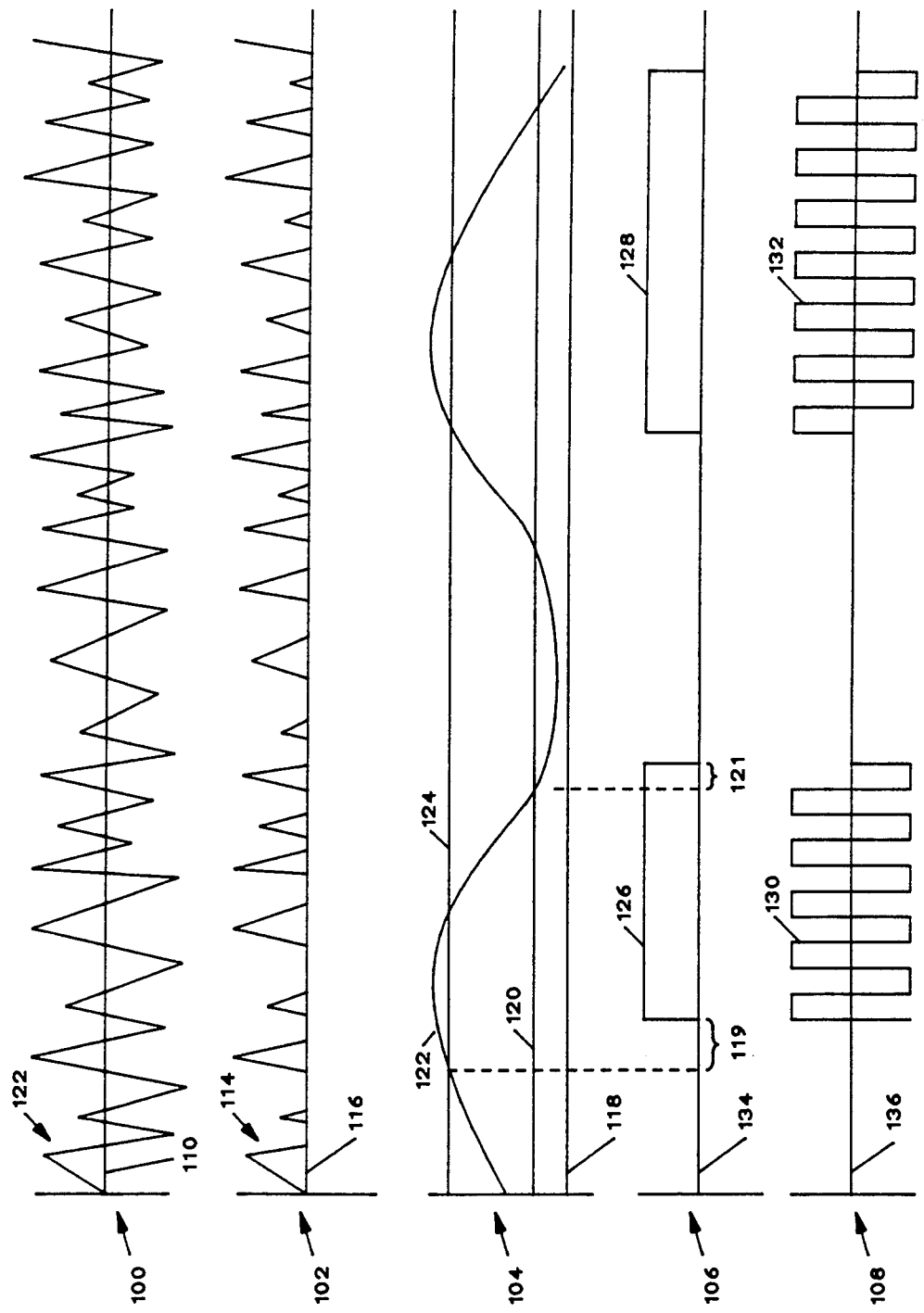
FIG. 4B is a graphical representation of the wave forms of various key signals within an alternative embodiment of the implantable pulse generator.

FIG. 4B is a graphical representation of key signals of the alternative embodiment of implantable pulse generator 150. The output of implantable pulse generator 150 is identical to the output of implantable pulse generator 20 except for programmable delay period 119 which is provided by programmable timer 59. All other referenced elements are as previously described.

Figure 5:
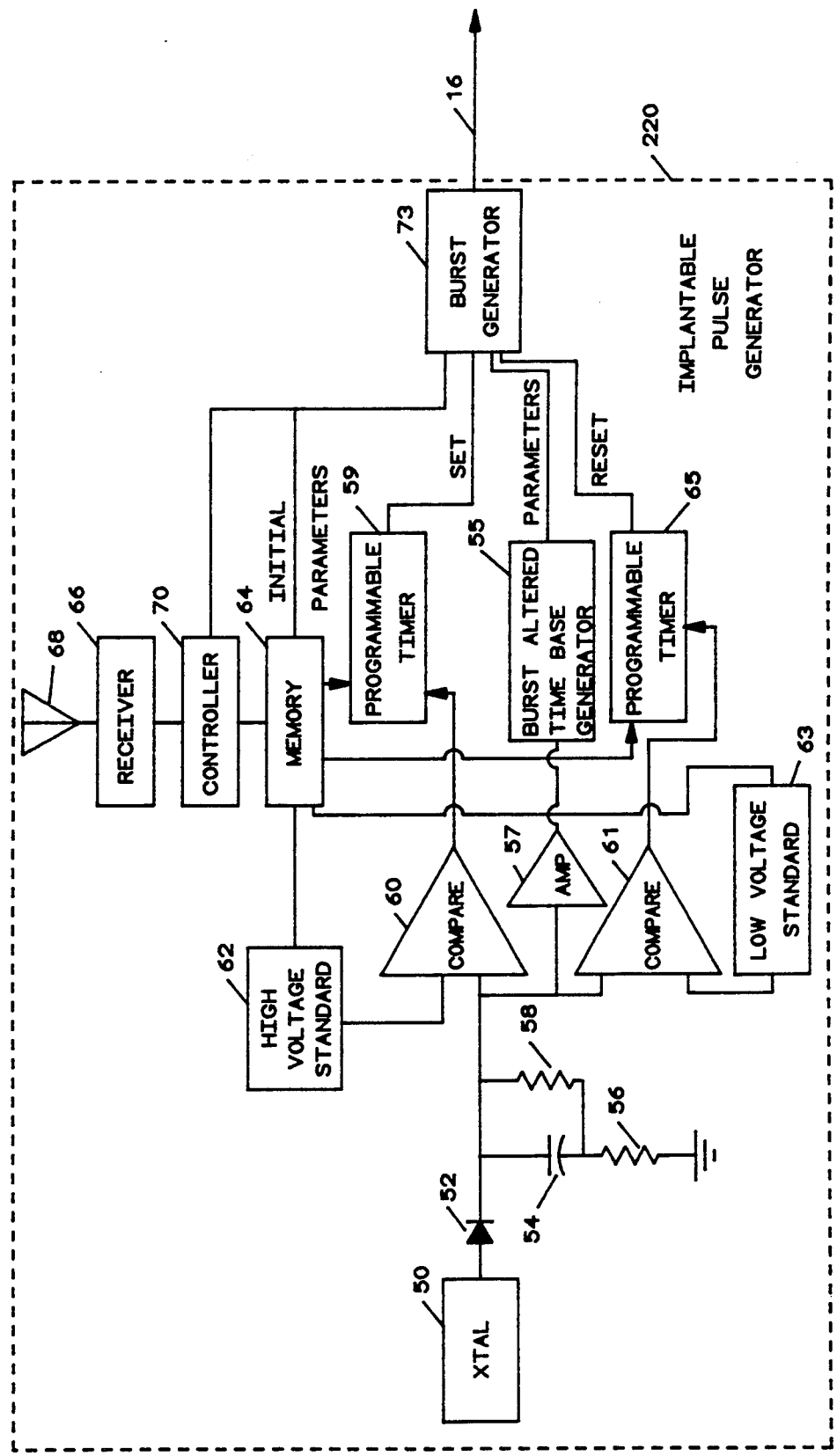
FIG. 5 is a block diagram of a second alternative embodiment.

FIG. 5 is a block diagram of the circuitry of a second alternative embodiment of implantable pulse generator 220. This circuitry is identical to that of implantable pulse generator 150 except that the output of burst generator 72 has parameters which are determined by the sensed activity level. To accomplish this amp 57 supplies the amplified and integrated sensor output to burst altered time base generator 55. The parameters are then supplied to program the output of burst generator 73.

Figure 6:
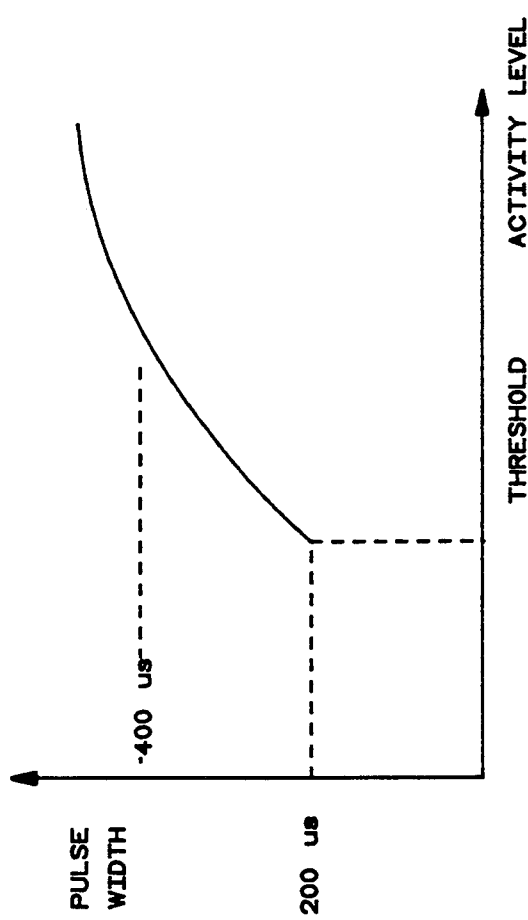
FIG. 6 is a graphical representation of the pulse width of the second alternative embodiment; and, FIG. 7 is a graphical representation of the output of the second alternative embodiment.

FIG. 6 is a graphical representation of change in one of the output parameters (e.g., pulse width) as a function of measured activity level.

Figure 7:
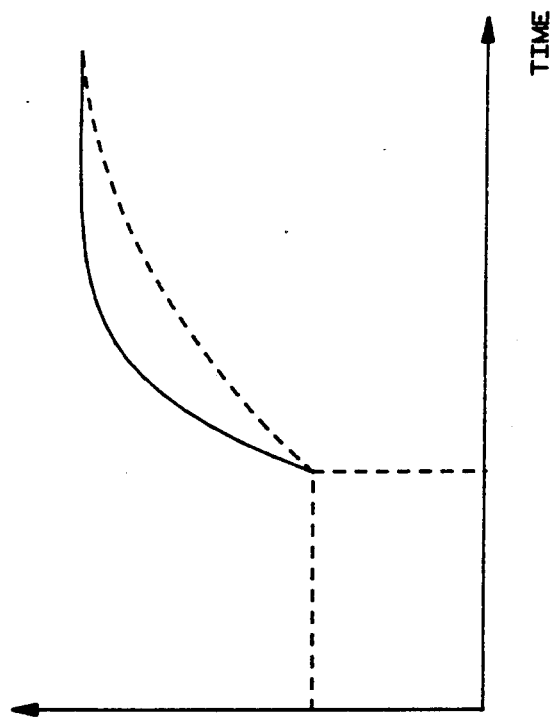

FIG. 7 is a graphical representation of the pulse width of the output of implantable pulse generator 220 as a function of time for a large increase in activity. The shape of the curve is influenced by the component values of the integrator circuit.

Those of skill in the art will readily appreciate that various other embodiments of the present invention may be made from the teachings found herein without deviating from the scope of the claims hereto attached.

I claim:

1. An apparatus comprising:
   a. a spinal cord electrode;
   b. a pulse generator electrically coupled to said spinal cord electrode;
   c. means coupled to said pulse generator for measuring cardiac requirements; and
   d. means coupled to said measuring means and said pulse generator for causing said pulse generator to produce stimulation signals whenever said cardiac requirements exceed a given threshold.

2. An apparatus according to claim 2 further comprising means for programming said given threshold.

3. An apparatus according to claim 2 wherein said programming means further comprises means for percutaneously programming said given threshold.

4. An apparatus according to claim 3 wherein said causing means further comprises an activity sensor.

5. A method of treating engine comprising:
   a. implanting an electrode in the spinal column of a patient;
   b. sensing the activity level of said patient; and,
   c. supplying bursts of stimulation energy to said electrode if said activity level of said patient as determined by said sensing step exceeds a threshold.

6. A method according to claim 5 further comprising discontinuing said supplying step if said sensing determines that said activity level has dropped below said threshold.

7. A method according to claim 6 further comprising delaying a predetermined amount of time between said sensing that said activity level has dropped below said threshold and said discontinuing of said supplying step.

* * * * *

UNITED STATES PATENT AND TRADEMARK OFFICE
CERTIFICATE OF CORRECTION

PATENT NO. : 5,058,584
DATED : October 22, 1991
INVENTOR(S) : Ivan Bourgeois

It is certified that error appears in the above—identified patent and that said Letters Patent is hereby corrected as shown below:

Column 6, line 10, the word "engine" should be changed to --angina--.

Signed and Sealed this

Sixteenth Day of February, 1993

Attest:

STEPHEN G. KUNIN

*Attesting Officer*  *Acting Commissioner of Patents and Trademarks*